United States Patent [19]

Ferris

[11] 4,432,993
[45] Feb. 21, 1984

[54] METHOD OF TREATING OBESITY HYPERGLYCEMIA, INFLAMMATION AND PLATELET AGGREGATION

[75] Inventor: Michael J. Ferris, Sutton, England

[73] Assignee: Beecham Group Limited, England

[21] Appl. No.: 305,117

[22] Filed: Sep. 24, 1981

[30] Foreign Application Priority Data

Sep. 26, 1980 [GB] United Kingdom ............... 8031228

[51] Int. Cl.³ ............................................. A61K 31/34
[52] U.S. Cl. ..................................... 424/285; 549/467
[58] Field of Search .................. 260/346.73; 424/285; 549/467

[56] References Cited

U.S. PATENT DOCUMENTS 3,452,052 6/1969 Binon et al. ............... 260/346.73
3,929,836 12/1975 Fothergill et al. ............. 260/346.73

FOREIGN PATENT DOCUMENTS 1061425 3/1967 United Kingdom .

Primary Examiner—Henry R. Jiles
Assistant Examiner—Bernard Dentz
Attorney, Agent, or Firm—Jacobs & Jacobs

[57] ABSTRACT

A compound of formula (I):

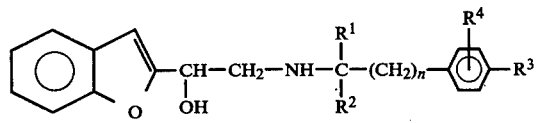

wherein
$R^1$ and $R^2$ are hydrogen or methyl,
$R^3$ is hydroxy, hydroxyalkoxy, benzyloxy or

X—Y—Z wherein (i)
X is a bond or oxygen,
Y is $C_{1-6}$ straight or branched alkylene, and
Z is hydrogen or carboxy;
or (ii)
X is a bond or moiety —O—CH$_2$—,
Y is $C_{2-6}$ straight or branched alkenylene, and
Z is carboxy; and
$R^4$ is an optional substituent, and n is 1, 2 or 3,
their esters, amides and salts, are anti-obesity, hypoglycaemic, anti-inflammatory and platelet aggregation inhibiting agents.

4 Claims, No Drawings

METHOD OF TREATING OBESITY HYPERGLYCEMIA, INFLAMMATION AND PLATELET AGGREGATION

The present invention relates to derivatives of 2-(2-benzofuranyl)ethanolamine which have anti-obesity, hypoglycaemic, anti-inflammatory and platelet-aggregation inhibiting activity, to processes for their production and to their use in medicine.

It has now been found that a series of 2-(2-benzofuranyl)ethanolamine derivatives have good hypoglycaemic, anti-inflammatory and platelet-aggregation inhibiting properties, increasing energy expenditure whilst having little cardiac stimulant activity.

Accordingly, the present invention provides a compound of formula (I)

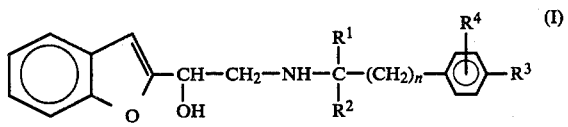

or an ester, amide or salt thereof, where appropriate, wherein
$R^1$ is hydrogen or methyl;
$R^2$ is hydrogen or methyl;
$R^3$ is hydroxy, hydroxy ($C_{1-6}$) alkoxy, benzyloxy or a group X—Y—Z
wherein:
(i) X is a bond or oxygen, Y is $C_{1-6}$ straight or branched alkylene, and Z is hydrogen or carboxy; or
(ii) X is a bond or moiety —O—CH$_2$—, Y is $C_{2-6}$ straight or branched alkenylene and Z is carboxy.
$R^4$ is selected from hydrogen, hydroxy, halogen, $C_{1-6}$ alkyl and $C_{1-6}$ alkoxy; and n is 1, 2 or 3.

In the case where the compound of formula (I) is an ester or amide, $R^3$ is suitably a group X—Y—COR$^5$ in which $R^5$ is $C_{1-6}$ alkoxy or $NR^6R^7$ and $R^6$ and $R^7$ are the same or different and each is selected from hydrogen and $C_{1-6}$ alkyl.

The $C_{1-6}$ alkyl and $C_{1-6}$ alkoxy groups mentioned above may each be straight or branched. Suitably such alkyl and alkoxy groups have from 1 to 4 carbon atoms, particular examples being methyl, ethyl, methoxy and ethoxy groups.

Suitably Y is a $C_{1-3}$ straight or branched alkylene, such as methylene or ethylene, or a $C_2$ or $C_3$ straight or branched alkenylene, such as ethenylene.

Preferably $R^1$ and $R^2$ are different, i.e. one is hydrogen and the other is methyl.

Most suitably $R^3$ is methyl or a group X—Y—COR$^5$ wherein $R^5$ is methoxy.

$R^4$ may be in any position on the phenyl ring. Suitably it is in the meta position relative to the ethanolamine moiety. Most suitably $R^4$ is a methyl or hydrogen substituent.

Preferably n is 1 or 2, most preferably 1.

Pharmaceutically acceptable salts of compounds of formula (I) include acid addition salts formed with a pharmaceutically acceptable acid such as hydrochloric acid, hydrobromic acid, orthophosphoric acid, sulphuric acid, methane sulphonic acid, toluenesulphonic acid, acetic acid, propionic acid, lactic acid, citric acid, fumaric acid, malic acid, succinic acid, salicylic acid or acetylsalicylic acid.

The salts and esters of compounds of formula (I) need not be pharmaceutically acceptable as they are also useful in the preparation of other compounds of formula (I) and in the separation of stereoisomers of compounds of formula (I) when the salt ion or ester radical is also optically active.

When $R^3$ is a group X—Y—$CO_2H$, the compounds of formula (I) may also be provided as pharmaceutically acceptable salts of the carboxylic acid. Such salts include alkali metal salts, alkaline earth metal salts and ammonium salts, preferably sodium, potassium, magnesium, calcium or ammonium salts.

Compounds of formula (I) have at least one asymmetric carbon atom, ie the one bearing the hydroxyl and benzofuranyl groups, and, when $R^1$ and $R^2$ are different, the carbon atom bearing $R^1$ and $R^2$ is also asymmetric. The compounds may, therefore, exist in at least two and often four stereoisomeric forms. The present invention encompasses all stereoisomers of the compounds of formula (I) whether free from other stereoisomers or admixed with other stereoisomers in any proportion and thus includes, for instance racemic mixtures of enantiomers.

Preferably, the carbon atom bearing the hydroxyl and benzofuranyl groups has the R configuration.

Preferably, the carbon atom bearing $R^1$ and $R^2$, when these are different, has the R configuration.

The most potent compounds of formula (I) are those wherein $R^1$ and $R^2$ are different and both asymmetric carbon atoms are in the R configuration.

The absolute configuration of any compound of formula (I) may be determined by conventional X-ray crystallographic techniques.

It is believed that, in the $^{13}C$ n.m.r. of compounds of formula (I) wherein one of $R^1$ and $R^2$ is hydrogen and the other is methyl, the diastereosomer having the greater anti-obesity activity is that for which the signal of the methyl group carbon atom appears at higher field (the lower numerical value when expressed in ppm) in $d_6$DMSO solution. The paired resonances often appear at approximately 20 ppm (less active) and slightly below 20 ppm (more active) down field from tetramethylsilane. Other paired resonances can occur for the carbon atoms attached directly to the nitrogen atom and the carbon which carries the hydroxyl and benzofuranyl groups. Again the paired resonances of the more active diastereomer of the investigated compounds appear at the higher field position.

Certain compounds of formula (I) have an alkenyl moiety (in $R^3$) and may, therefore, exist in both E and Z geometrical isomeric forms. The present invention encompasses both E and Z isomers of such compounds, whether in the isomerically pure state or admixed in any proportions.

Preferably, compounds of formula (I) having an alkenyl moiety in $R^3$ are in the E configuration.

The present invention also provides a process for producing a compound of formula (I) by reducing a compound of formula (II)

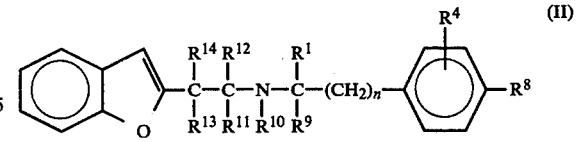

wherein $R^1$, $R^4$ and n are as defined in relation to formula (I);
$R^8$ is a group $R^3$ as defined in relation to formula (I) or alkoxycarbonylalkoxy;
$R^9$ is a group $R^2$ as defined in relation to formula (I) or together with $R^{10}$ forms a bond;
$R^{10}$ is hydrogen, benzyl or together with $R^9$ or $R^{11}$ forms a bond;
$R^{11}$ is hydrogen or together with $R^{12}$ forms an oxo-group or together with $R^{10}$ forms a bond;
$R^{12}$ is hydrogen or together with $R^{11}$ forms an oxo-group;
$R^{13}$ is hydroxyl or together with $R^{14}$ forms an oxo-group;
$R^{14}$ is hydrogen or together with $R^{13}$ forms an oxo-group.

Provided that there is no more than one oxo-group and no more than one bond represented by any of $R^9$ to $R^{14}$, and optionally thereafter forming a salt, ester or amide of the compound of formula (I) so formed and/or converting the compound of formula (I) so formed into a further compound of formula (I).

When there are two or more reducible moieties in the compound of formula (II) these may, generally, be reduced separately in any order or simultaneously. However, when $R^8$ is an alkenylene group, or contains an alkenylene group, the double bond thereof may be reduced at the same time as any reducible moiety elsewhere in the molecule. When $R^8$ is an alkoxycarbonylalkoxy group this may be reduced simultaneously with or separately to the reduction of other reducible moieties in the molecule.

The aforementioned reductions may be effected by conventional chemical or catalytic methods, such as chemical reduction using a complex hydride such as lithium aluminium hydride, sodium cyanoborohydride or sodium borohydride or aluminium amalgam or by catalytic hydrogenation using catalysts such as palladium on charcoal, or platinum, for instance, as platinum oxide, except when $R^8$ has an alkenylene group, as this will be reduced simultaneously.

Catalytic hydrogenation is conveniently effected using hydrogen gas at about 1 atmosphere pressure when platinum is used as catalyst and at medium to high pressure, conveniently 50 to 100 psi, when a palladium catalyst is used. Such hydrogenations may be conducted in conventional hydrogenation solvents such as a lower alkanol, for instance ethanol and at any convenient, non-extreme temperature. It is generally most suitable to use a slightly raised temperature such as 30° C. to 100° C., for example 40° C. to 80° C.

The desired compound may be isolated from the reaction mixture by evaporation of the filtered solution. The initially obtained product may be purified by conventional means, for example by chromatography, crystallisation or the like.

Reduction by sodium borohydride is conveniently effected in a lower alkanolic solvent such as methanol. The reaction is generally carried out at a temperature of, for example, 20° to 30° C.

Reduction by lithium aluminium hydride is conveniently effected in a dry, ether solvent such as diethyl ether or tetrahydrofuran at ambient or elevated temperature.

The desired compound may be obtained by hydrolysis of the reaction mixture, extraction into a suitable solvent such as ethyl acetate and evaporation. The initially obtained product may be purified as outlined hereinbefore.

In particular aspects, the present invention provides processes for producing compounds of formula (I) by reducing a compound of formula (IIA):

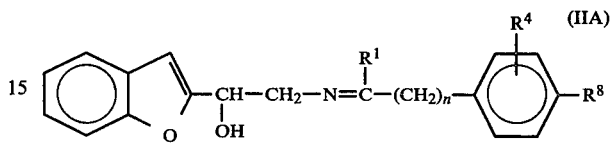

or reducing a compound of formula (IIB):

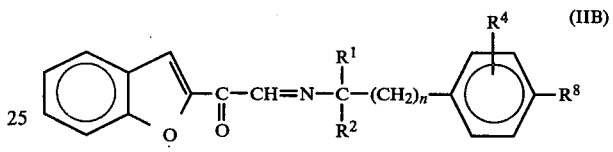

or reducing a compound of formula (IIC):

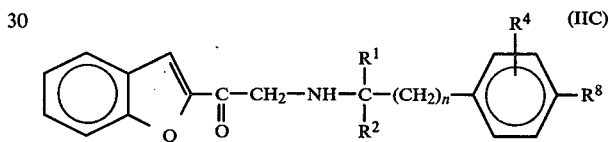

or the N-benzyl derivative thereof, or reducing a compound of formula (IID):

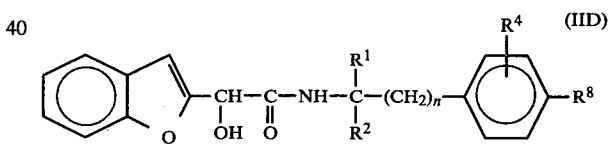

or reducing a compound of formula (IIE):

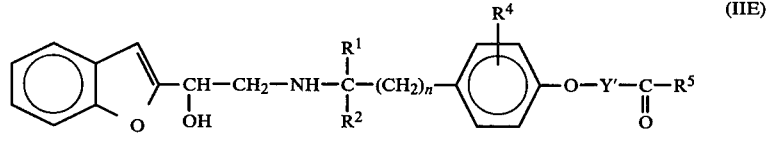

or reducing a compound of formula (IIF):

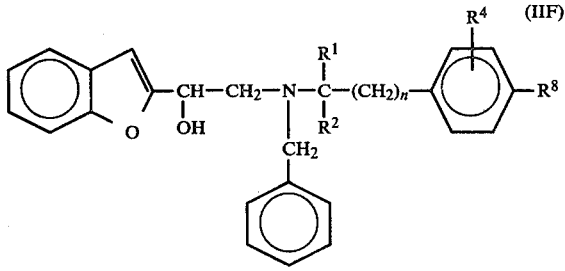

or reducing a compound of formula (IIG):

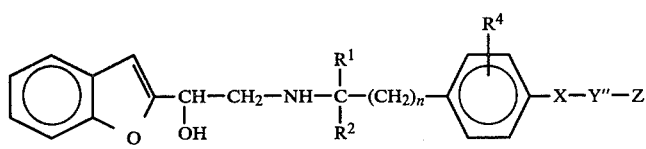

wherein
$R^1$, $R^2$, $R^4$, $R^5$, $R^8$, n, X and Z are as defined in relation to formulae (I) and (II);
Y' is $C_{1-6}$ straight or branched alkylene; and
Y'' is $C_{2-6}$ straight or branched alkenylene.

The present invention also provides a process for producing a compound of formula (I) by reacting a compound of formula (III):

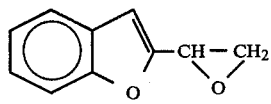

with a compound of formula (IV):

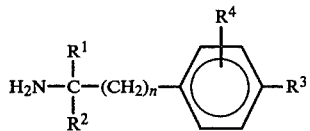

or a salt, ester or amide thereof, wherein $R^1$, $R^2$, $R^3$, $R^4$ and n are as defined in relation to formula (I); and optionally thereafter forming a salt, ester or amide of the compound of formula (I) so formed and/or converting the compound of formula (I) so formed into a further compound of formula (I).

This reaction is conveniently effected in a solvent such as a lower alkanol, preferably ethanol.

Esters, amides and salts of compounds of formula (I) may be produced directly using the appropriate compound of formula (II) or may be produced from the free acid of formula (I) by conventional means. Free acids of formula (I) may be obtained directly or by cleavage of the corresponding ester or amide, or from the corresponding salt by conventional means.

The compounds of formula (I) so produced may be purified by conventional means such as crystallisation and/or chromatography.

Those compounds of formula (I) having only one asymmetric carbon atom (i.e. when $R^1$ and $R^2$ are the same) may, if desired, be resolved into enantiomers by conventional means, for example by the use of an optically active acid as a resolving agent. Those compounds of formula (I) having two asymmetric carbon atoms may be separated into diastereomeric pairs of enantiomers by, for example, fractional crystallisation from a suitable solvent such as ethyl acetate or benzene. The pair of enantiomers thus obtained may be separated into individual stereoisomers by conventional means such as by the use of an optically active acid as a resolving agent.

Suitable optically active acids which may be used as resolving agents are described in "Topics in Stereochemistry" Vol 6, Wiley Interscience, 1971; Allinger N L and Eliel, W. L. (Eds).

Any desired enantiomer of a compound of formula (I) may be obtained by stereospecific synthesis using optically pure starting materials of known configuration.

Thus, by using single enantiomers of the compounds of formula (III) and (IV) a required enantiomer of the corresponding compound of formula (I) can be obtained. Similarly, the reaction of a single enantiomer of a compound of formula (V) with a single enantiomer of formula (VIC) below will result in a single enantiomer of a compound of formula (IID) above. The latter may be reduced to a compound of formula (I) without altering the stereochemical configuration thereby affording a single enantiomer of the compound of formula (I). Reaction of a compound of formula (V) with a single enantiomer of a compound of formula (VID) will give a single enantiomer of a compound of formula (I) directly. Thus, for instance, the R enantiomer of a compound of formula (VID) or (VIC), when reacted with the R enantiomer of a compound of formula (V) directly or indirectly affords the RR enantiomer of the desired compound of formula (I).

Many of the reductions described in relation to compounds of formula (II) directly involve the asymmetric, or potentially asymmetric carbon atoms and consequently result in the formation of mixtures of stereoisomers. Thus reduction of a single enantiomer of a compound of formula (IIA), (IIB) or (IIC) will result in the formation of a pair of enantiomers of a corresponding compound of formula (I) whereas reduction of a racemic mixture of enantiomers of a compound of formula (IIA) (IIB) or (IIC) will result in the formation of a mixture of all four enantiomers of the corresponding compound of formula (I). Such mixtures may be separated into pairs of enantiomers and/or resolved into single enantiomers as described above.

Compounds of formula (II) may be produced by reacting a compound of formula (V):

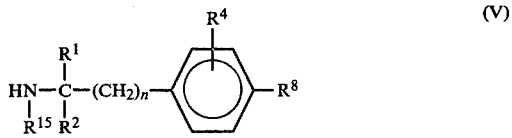

or a salt, ester or amide thereof, wherein $R^1$, $R^2$, $R^4$, $R^8$ and n are as defined in relation to formulae (I) and (II), and $R^{15}$ is hydrogen or benzyl, with a compound of formula (VI):

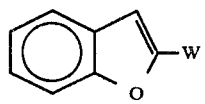   (VI)

wherein W is a reactive moiety which is capable of reacting with the amine of formula (V) thus forming a compound of formula (II). Typical examples of compounds of formula (VI) are:

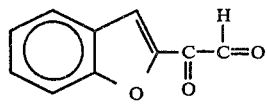   (VIA)

or its hydrate or hemiacetal of a lower alkanol;

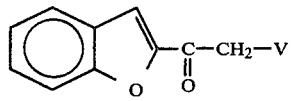   (VIB)

wherein V is a halogen atom, preferably bromine;

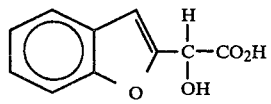   (VIC)

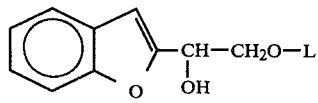   (VID)

wherein O—L is a leaving group, preferably tosyloxy.

and 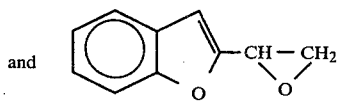   (III)

It will be appreciated that when $R^8$ is a group $R^3$ and $R^{15}$ is hydrogen, the reaction of a compound of formula (V) with the compound of formula (VID) or (III) produces a compound of formula (I) directly, the latter being identical to the reaction between compounds of formulae (III) and (IV) above.

Conventional conditions suitable for use with the particular compound of formula (VI) may be used for this reaction. Thus the reaction of a compound of formula (VIA) with a compound of formula (V) is conveniently conducted at elevated temperature under conditions resulting in the removal of the water formed during the reaction. A particularly suitable method is to perform the reaction in a solvent such as benzene, under reflux and azeotropically to remove the water using a Dean and Stark trap.

The reaction of a compound of formula (VIB) with a compound of formula (V) is conveniently conducted in a polar organic solvent such as acetonitrile or butanone, at an elevated temperature, for instance under reflux.

The reaction of a compound of formula (VIC) with a compound of formula (V) is conveniently conducted under standard peptide formation reaction conditions.

The reaction of a compound of formula (VID) with a compound of formula (V) is conveniently conducted in a solvent such as dimethyl sulphoxide at elevated temperature, preferably 50° C. for about 3 days.

The reaction of a compound of formula (III) with a compound of formula (V) is conveniently conducted in a solvent such as a lower alkanol, preferably ethanol.

Certain compounds of formula (II) may also be produced by reacting a compound of formula (VII):

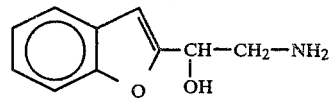   (VII)

with a compound of formula (VIII):

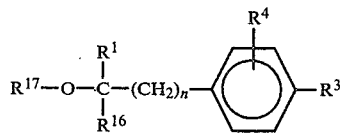   (VIII)

or a salt, ester or amide thereof, wherein
$R^1$, $R^3$, $R^4$ and n are as defined in relation to formula (I)
$R^{16}$ is a group $R^2$ or together with $R^{17}$ forms a bond, and
$R^{17}$ is a group L such that O—L is a leaving group, preferably tosyloxy, or together with $R^{16}$ forms a bond.

The reaction of a compound of formula (VII) with a ketone of formula (VIII) is conveniently effected under conditions which result in the removal of water formed during reaction. A particularly suitable method is to perform the reaction in a solvent, such as benzene, under reflux and azeotropically to remove the water using a Dean and Stark trap.

The reaction of a compound of formula (VII) with a compound of formula (VIII) wherein $R^{17}$ is a group L is conveniently effected in a solvent such as dimethylsulphoxide at elevated temperature, preferably at about 50° C. for about two to three days.

It is often convenient to prepare the compound of formula (II) and then use it in situ without isolation to produce the required compound of formula (I).

The intermediates of formulae (III), (IV), (V), (VI) and (VII) may be produced by conventional methods.

In another aspect of the present invention there are provided the compounds of formula (II), (III), (VI) or (VII) as hereinbefore defined. Such compounds are useful as intermediates in the production of compounds of formula (I).

A compound of formula (I), or pharmaceutically acceptable salt, ester or amide thereof, where appropriate, (hereinafter "the drug") may be administered as the pure drug, however, it is preferred that the drug be administered as a pharmaceutical composition also comprising a pharmaceutically acceptable carrier.

Accordingly, the present invention also provides a pharmaceutical composition comprising a compound of formula (I) or a pharmaceutically acceptable salt, ester or amide thereof, where appropriate, in association with a pharmaceutically acceptable carrier therefor.

As used herein the terms "pharmaceutical composition" and "pharmaceutically acceptable" embrace compositions and ingredients for both human and/or veterinary use.

Usually the compositions of the present invention will be adapted for oral administration although compositions for administration by other routes, such as by injection are also envisaged. For use as an anti-inflammatory agent compounds of the present invention are, preferably, formulated as topical compositions.

Particularly suitable compositions for oral administration are unit dosage forms such as tablets and capsules. Other fixed-unit dosage forms, such as powders presented in sachets, may also be used.

In accordance with conventional pharmaceutical practice the carrier may comprise a diluent, binder, filler, disintegrant, wetting agent, lubricant, colourant, flavourant or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 500 mg, more usually 0.1 to 250 mg and favourably 0.1 to 100 mg. Such doses may be taken one to six times a day in a manner such that the total daily dose for a 70 kg adult will generally be about 0.1 to 1000 mg and more usually about 1 to 500 mg.

In addition to use in human medicine the compositions of this invention may be used to treat obesity, hyperglycaemia, inflammation and to inhibit platelet aggregation in domestic mammals such as dogs. In general, administration to domestic mammals may be by mouth and will usually take place one or two times a day at about 0.025 mg/kg to 2.5 mg/kg, for example 0.1 mg/kg to 2 mg/kg.

The present invention further provides a method for treating obesity in humans or domestic mammals comprising administering an effective, non-toxic amount of a compound of formula (I) or a pharmaceutically acceptable salt, ester or amide thereof, where appropriate, or of a composition thereof as hereinbefore defined to an obese human or domestic mammal.

The present invention also provides a method for treating hyperglycaemia in humans or domestic mammals comprising administering an effective, non-toxic amount of a compound of formula (I) or a pharmaceutically acceptable salt, ester or amide thereof, where appropriate, or of a composition thereof as hereinbefore defined, to a hyperglycaemic human or domestic mammal.

The present invention further provides a method for treating inflammation in humans and domestic mammals comprising administering an effective, non-toxic amount of a compound of formula (I) or a pharmaceutically acceptable salt, ester or amide thereof, where appropriate, or of a composition thereof as hereinbefore defined, to a human or domestic mammal suffering from inflammation.

The present invention also provides a method for inhibiting platelet aggregation in humans and domestic mammals in need of such treatment, comprising administering an effective, non-toxic amount of a compound of formula (I) or a pharmaceutically acceptable salt, ester or amide thereof, or of a composition thereof as hereinbefore defined.

The invention will now be illustrated by reference to the following Examples, which are not intended to limit the invention in any way. The preparation of intermediates is described in the Description.

EXAMPLE 1

N-[2-(4-Methylphenyl)-1-methylethyl]-2-(2-benzofuranyl)-2-hydroxy ethanamine

A mixture of 2-(2-benzofuranyl)-2-hydroxy ethanamine (1.0 g) and 4-methylphenylacetone (0.76 g) in benzene (50 ml) was heated under reflux using a Dean and Stark head until the required amount of water had been collected. The solvent was evaporated, replaced with ethanol (50 ml) and the solution hydrogenated at atmospheric pressure over platinum oxide until the theoretical amount of hydrogen had been taken up. The reaction mixture was filtered through diatomaceous earth, the filtrate evaporated and the residue chromatographed on Kieselgel 60. Elution with 2% methanol-chloroform gave N-[2-(4-methylphenyl)-1-methylethyl]-2-(2-benzofuranyl)-2-hydroxy ethanamine, as an 80:20 mixture of diastereoisomers, m.p. 92–98 (cyclohexane).

1H nmr $\tau$ (CDCl$_3$): 9.05 (3H, d, J=6 Hz), 7.75 (3H, s), 6.9–7.4 (5H, m), 6.5–7.0 (2H, broad), 5.27 (1H, t, J=6 Hz), 3.3 (1H, s), 3.0 (4H, s) 2.9–2.7 (2H, m) 2.4–2.6 (2H, m).

EXAMPLE 2

N-[2-(4-[(E)-2-Carbomethoxyethenyl]phenyl)-1-methylethyl]-2-(2-benzofuranyl)-2-hydroxyethanamine A mixture of 2-(2-benzofuranyl)-2-hydroxyethanamine (1.0 g) and 4-[(E)-2-carbomethoxyethenyl]phenyl propan-2-one (1.13 g) was heated under reflux using a Dean and Stark head until the theoretical amount of water had been removed. The solvent was evaporated, the residue dissolved in methanol (50 ml) and sodium borohydride (0.5 g) added. The solvent was evaporated, the residue partitioned between water and ethyl acetate and the organic layer dried (magnesium sulphate). Removal of the solvent gave an oil which was chromatographed on Kieselgel 60. Elution with 2% methanol-chloroform gave N-[2-(4-[(E)-2-carbomethoxyethenyl]-phenyl)-1-methylethyl]-2-(2-benzofuranyl)-2-hydroxyethanamine, as a 54:46 mixture of diastereoisomers, m.p. 85–89 (cyclohexane).

1H nmr $\tau$ (CDCl$_3$): 9.05 (3H, d, J=6 Hz), 7.0–7.5 (5H, m), 6.75 (1H, s, replaceable with D$_2$O), 6.3 (3H, s), 5.3 (1H, m), 4.5 (1H, broad, replaceable with D$_2$O), 3.5 (1H, d, J=15 Hz), 3.33 (1H, s), 2.8 (4H, m), 2.5 (4H, m), 2.4 (1H, d, J=15 Hz).

EXAMPLE 3

N-[2-(4-Carbomethoxymethoxyphenyl)-1-methylethyl]-2-(2-benzofuranyl)-2-hydroxyethanamine By a method exactly analogous to that described in Example 2 but using 2-(2-benzofuranyl)-2-hydroxyethanamine (1.3 g) and 4-carbomethoxymethoxyphenylpropan-2-one (1.63 g), N-[2-(4-carbomethoxymethoxyphenyl)-1-methylethyl]-2-(2-benzofuranyl)-2-hydroxyethanamine was prepared (0.25 g) as a 55:45 mixture of diastereoisomers, m.p. 79–87 (hexane).

1H nmr τ (CDCl₃): 8.95 (3H, d, J=6 Hz), 6.5-7.8 (7H, m, 2H replaceable by D₂O), 6.18 (3H, s), 5.42 (2H, m), 5.2 (1H, m), 3.4 (1H, s), 2.3-3.5 (8H, m).

EXAMPLE 4

N-[2-(4-(3-Carbomethoxypropoxy)phenyl)-1-methylethyl]-2-(2-benzofuranyl)-2-hydroxyethanamine By a method analogous to that described in Example 2 but using 2-(2-benzofuranyl)-2-hydroxyethanamine (4.54 g) and 1-(4-[3-carbomethoxypropoxy]phenyl)propan-2-one (6.41 g), N-[2-(4-(3-carbomethoxyphenoxy)phenyl)-1-methylphenyl]-2-(2-benzofuranyl)-2-hydroxyethanamine was prepared, m.p. 63°–70° (Et₂O) as a 37:63 mixture of diastereoisomers.

1H nmr τ (CDCl₃): 8.95 (3H, d), 6.8-8.2 (11H, complex), 6.35 (3H, s), 6.1 (2H, t), 5.2 (1H, m), 2.35-3.5 (9H, complex).

EXAMPLE 5

Preparation of (RR,SS) and RS,SR) (N-[2-(4-methylphenyl)-1-methylethyl]-2-(2-benzofuranyl)-2-hydroxyethanamine A mixture of 2-benzofuran glyoxal (10.44 g) and 2-amino-3-(4-methylphenyl)propane (8.94 g) was refluxed in benzene using a Dean and Stark head until the theoretical amount of water had been removed. The solvent was evaporated, replaced with methanol and sodium borohydride (5 g) added. The methanol was evaporated, the residue partitioned between water and ether and the ether layer dried. Filtration and evaporation gave an oil which was chromatographed on Kieselgel 60. Elution with 2% methanol-chloroform gave N-[2-(4-methylphenyl)-1-methylethyl]-2-(2-benzofuranyl)-2-hydroxyethanamine (14 g).

Recrystallisation of this material twice from benzene yielded the (RS, SR) diastereoisomer in 96% diastereomeric purity (2.4 g), m.p. 114-120. Evaporation of the original mother liquor and recrystallisation of the solid three times from hexane gave 1.3 g, m.p. 88°–100°, of 72% (RR,SS) material. Recrystallisation of this from benzene gave the (RR,SS) diastereoisomer (0.52 g) m.p. 102°–105° in 90% diastereomeric purity.

1H nmr identical with that described in Example 1.

EXAMPLE 6

N-[2-(4-Methylphenyl)ethyl]-2-(2-benzofuranyl)-2-hydroxyethanamine

By a method analogous to that described in Example 5 but using 2-(4-methylphenyl)ethylamine (3.39 g) and 2-benzofuranglyoxal (3.08 g), N-[2-(4-methylphenyl)ethyl]-2-(2-benzofuranyl)-2-hydroxyethanamine m.p. 112°–113° (ethyl acetate) was prepared.

1H nmr τ (CDCl₃): 7.7 (3H, s), 7.5 (2H, broad, disappears with D₂O), 7.05-7.4 (4H, m), 6.95 (2H, d, J=6 Hz), 5.2 (1H, t, J=6 Hz), 3.4 (1H, s), 2.95 (4H, s), 2.4-2.9 (4H, m).

EXAMPLE 7

N-[3-(4-Methylphenyl)-1-methylpropyl]-2-(2-benzofuranyl)-2-hydroxyethanamine

By a method analogous to that described in Example 2 but using 2-(2-benzofuranyl)-2-hydroxyethanamine (2.03 g) and 4-(4-methylphenyl)butan-2-one (2.04 g), N-[3-(4-methylphenyl)-1-methylpropyl]-2-(2-benzofuranyl)-2-hydroxyethanamine, m.p. 83°–84° (hexane) was prepared as a 1:1 mixture of diastereoisomers.

1H nmr τ (CDCl₃): 8.9 (3H, d, J=6 Hz), 8.15-8.65 (2H, m), 7.7 (3H, s), 7.1-7.6 (5H, m, includes 2H replaceable by D₂O), 7.0 (2H, m), 5.2 (1H, t, J=6 Hz), 3.35 (1H, s), 2.9 (4H, s), 2.4-2.9 (4H, m).

EXAMPLE 8

N-[3-(4-Methylphenyl)-1,1-dimethylpropyl]-2-(2-benzofuranyl)-2-hydroxyethanamine By a method analogous to that described in Example 5 but using 2-benzofuranyl glyoxal (2.65 g) and 4-(4-methylphenyl)-2-amino-2-methylbutane (3.0 g), N-[3-(4-methylphenyl)-1,1-dimethylpropyl]-2-(2-benzofuranyl)-2-hydroxyethanamine, m.p. 121°–122° (ether) was prepared.

1H nmr τ (CDCl₃): 8.9 (6H, s), 8.3-8.6 (2H, m), 7.8 (3H, s), 7.3-7.65 (2H, m), 7.0-8.0 (2H, disappears with D₂O), 7.0 (2H, d, J=6 Hz), 5.3 (1H, t, J=6 Hz), 3.4 (1H, s), 2.9 (4H, s), 2.4-2.9 (4H, m).

EXAMPLE 9

N-[2-(4-Methylphenyl)-1,1,dimethylethyl]-2-(2-benzofuranyl)-2-hydroxyethanamine

By a method analogous to that described in Example 5 but using 2-benzofuranyl glyoxal (3.2 g) and 3-(4-methylphenyl)-2-amino-2-methylpropane (3.0 g), N-[2-(4-methylphenyl)-1,1-dimethylethyl]-2-(2-benzofuranyl)-2-hydroxyethanamine, m.p. 95°–100° (cyclohexane) was prepared.

1H nmr τ (CDCl₃): 8.9 (3H, s), 8.85 (3H, s), 7.3 (3H, s), 7.4 (2H,s), 6.7-7.5 (2H, broad), 6.95 (2H, d, J=5 Hz), 5.25 (1H, t, J=6 Hz), 3.35 (1H, s), 2.95 (4H, s), 2.4-2.85 (4H, m).

EXAMPLE 10

N-[3-(4-Methylphenyl)propyl]-2-(2-benzofuranyl)-2-hydroxyethanamine

A mixture of 2-(2-benzofuranyl)-2-hydroxyethanamine (1.75 g), 3-(4-methylphenyl)-1-(4-methylphenylsulphonyloxy) propane (3.0 g) and triethylamine (1.5 g) was stirred in dimethylsulphoxide for 2 days at ambient temperature. The mixture was poured into water, extracted with ether and the ether layers dried. Removal of the solvent gave an oil which was crystallised and recrystallised from ether to give N-[3-(4-methylphenyl)propyl]-2-(2-benzofuranyl)-2-hydroxyethanamine m.p. 118°–119°.

1H nmr τ (CDCl₃): 8.0-8.35 (2H m), 7.7 (3H, s), 7.1-7.7 (6H, m, including 2H replaceable with D₂O), 6.95 (2H, d, J=6 Hz), 5.15 (1H, t, J=6 Hz), 3.35 (1H, s), 2.95 (4H, s), 2.4-2.9 (4H, m).

EXAMPLE 11

N-[2-(4-Hydroxyethoxyphenyl)-1-methylethyl]-2-(2-benzofuranyl)-2-hydroxyethanamine A mixture of 1-(4-carbomethoxymethoxyphenyl)-propan-2-one (1 g) and 2-(2-benzofuranyl)-2-hydroxyethanamine (0.8 g) in benzene (80 ml) was boiled under reflux for one hour, with azeotropic removal of water, using a Dean and Stark head. The solution was evaporated, the residue dissolved in methanol (80 ml), cooled in ice, and excess sodium borohydride added. The solution was stirred at ambient temperature for 1 hour, heated under reflux for one hour, the methanol evaporated and the residue partitioned between water and ethyl acetate. The dried organic extract was evaporated to give an oil which was chromatographed on silica gel in 4% methanol/dichloromethane. The resulting oil was treated with ethereal hydrogen chloride to give the title compound as the hydrochloride salt hemi-hydrate, isolated as a 50:50 mixture of diastereoisomers. (mpt 56°–65°) (Ethyl Acetate-Ether).

1H nmr τ (CDCl$_3$)—Free Base: 8.9 (3H, d, J=6 Hz), 6.85–7.85 (7H, m, 2H replaceable by D$_2$O), 6.0 (4H, s), 5.15 (1H, m), 2.33–3.35 (9H, m).

EXAMPLE 12

N-[2-(4-Carbomethoxymethoxy-3-methylphenyl)-1-methylethyl]2-(2-benzofuranyl)-2-hydroxyethanamine By a method analogous to that described in Example 1 but using 2-(2-benzofuranyl)-2-hydroxyethanamine (0.75 g) and 1-(4-carbomethoxymethoxy-3-methylphenyl)propan-2-one (1.0 g), N-[2-(4-carbomethoxymethoxy-3-methylphenyl)-1-methylethyl]-2-(2-benzofuranyl)-2-hydroxyethanamine was prepared, m.p. 115°–30° (Et$_2$O) as a 38:62 mixture of diastereoisomers.

1H nmr τ (CDCl$_3$): 8.9 (3H, d), 7.8 (3H, s), 6.8–7.7 (7H, m), 6.25 (3H, s), 5.4 (2H, s), 5.2 (1H, m), 2.2–3.5 (8H, complex).

EXAMPLE 13

N-[2-(4-Hydroxyphenyl)-1-methylethyl]-2-(2-benzofuranyl)-2-hydroxyethanamine

N-[2-(4-Benzoyloxyphenyl)-1-methylethyl]-2-(2-benzofuranyl)-2-hydroxyethanamine (2 g) in ethyl acetate (150 ml) was hydrogenated over 5% palladium on charcoal at atmospheric pressure. After uptake of hydrogen had ceased the mixture was filtered and the filtrate evaporated to dryness. Chromatography of the residual oil on Kieselgel 60 (5% methanol in dichloromethane) gave the title compound, m.p. 135°–8°, (EtOAc-ether), as a 94:6 mixture of diastereoisomers.

1H nmr τ (DMSO d$_6$): 9.05 (3H, d), 6.8–7.9 (8H, complex), 5.25 (1H, m), 2.3–3.5 (9H, complex).

EXAMPLE 14

N-[2-(4-Benzyloxyphenyl)-1-methylethyl]-2-(2-benzofuranyl)-2-hydroxyethanamine

This was prepared in an identical manner to the compound described in Example 2 using 2-(2-benzofuranyl)-2-hydroxyethanamine (3.51 g) and 1-(4-benzyloxyphenyl)propan-2-one (4.75 g). Chromatography of the residual oily solid on Kieselgel 60 (4% methanol in dichloromethane) gave the title compound, m.p. 111°–122°, as a 20:80 mixture of diastereoisomers.

1H nmr τ (CDCl$_3$): 8.95 (3H, d), 6.7–7.6 (7H, m), 4.9–5.35 (3H, s superimposed on m), 2.3–3.5 (14H, complex).

EXAMPLE 15

N-[2-(4-Methoxyphenyl)-1-methylethyl]-2-(2-benzofuranyl)-1-hydroxyethanamine

This compound was prepared in an identical manner to the compound described in Example 2 using 2-(2-benzofuranyl)-2-hydroxyethanamine (1.65 g) and 1-(4-methoxyphenyl)propan-2-one (1.53 g). Chromatography of the residual oil on Kieselgel 60 (4% methanol in dichloromethane) gave the title compound, m.p. 75°–85° (Et$_2$O-hexane) as a 44:56 mixture of diastereoisomers.

1H nmr τ (CDCl$_3$): 8.95 (3H, d), 6.8–7.6 (7H, complex), 6.25 (3H, s), 5.2 (1H, m), 2.35–3.5 (9H, complex).

DESCRIPTION 1

2-(2-benzofuranyl)-2-hydroxyethanamine

Trimethylsilylcyanide (1.63 g, 2 ml) was added to a solution of 2-formylbenzofuran (2.0 g), (prepared as described in French Pat. No. 1.537.206) and a trace of zinc iodide in dry ether (50 ml) at 0° under nitrogen. The reaction mixture was stirred under nitrogen at ambient temperature for 10 h. This solution was then added dropwise to a suspension of lithium aluminium hydride (0.63 g) in dry ether under nitrogen. The mixture was heated under reflux for 1 h at the end of the addition. The reaction mixture was cooled; water (0.63 ml), 2 M sodium hydroxide (0.63 ml) and more water (1.89 ml) added, the reaction mixture filtered, the residue washed with chloroform and the combined solvents evaporated to give 2-(2-benzofuranyl)-2-hydroxyethanamine, (1.58 g).

1H nmr τ (CDCl$_3$): 7.9 (3H, broad, replaceable with D$_2$O), 6.85 (2H, broad), 5.27 (1H, t, J=5 Hz), 3.4 (1H, s), 2.9–2.4 (4H, m).

DEMONSTRATION OF EFFECTIVENESS OF COMPOUNDS (I) Anti-Obesity Activity

The compounds were administered by oral gavage in water or carboxymethyl-cellulose suspension to genetically obese mice daily for 28 days. At the end of the time the carcass composition was determined. The results obtained were as follows:

| COMPOUND OF EXAMPLE NO. | DOSE mg/kg p.o. | g LIPID/MOUSE TREATED | g LIPID/MOUSE CONTROL |
|---|---|---|---|
| *1 | 4.8 | 13.36 | 16.25 |
| 5 mp 102–5 | 4.8 | 16.16 | 21.10 |
| 10 | 8.6 | 19.72 | 23.13 |

*15 days only (II) Effect on Energy Expenditure

The effect of the compounds on the energy expenditure of mice was demonstrated by means of the following procedure.

Female CFLP mice each weighing approximately 24 g were give food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content following the principles described by J. B. de V. Weir, *J. Physiol.* (London) 109, 1–9, (1949). The food intake of the mice was measured over this same period of 21 hours. The results are expressed as a percentage of the mean food intake or rate of energy expenditure of the mice dosed with water.

| COMPOUND OF EXAMPLE NO. | DOSE (mg/kg po) | MEAN ENERGY EXPENDITURE (%) 0-3 h | 0-21 h | MEAN FOOD INTAKE (%) |
| --- | --- | --- | --- | --- |
| Control | | 100 | 100 | 100 |
| 1 | 17 | 175 | 134 | 107 |
| 2 | 21 | 152 | 115 | 107 |
| 3 | 21 | 174 | 120 | 88 |
| 4 | 22.9 | 135 | 105 | 70 |
| 5 mpt 114–20 | 8.6 | 139 | 110 | 93 |
| 5 mpt 102–5 | 8.6 | 153 | 123 | 91 |
| 6 | 16.4 | 156 | 105 | 103 |
| 7 | 17.9 | 138 | 120 | 113 |
| 8 | 18.8 | 130 | 105 | 108 |
| 9 | 17.9 | 117 | 109 | 102 |
| 10 | 17.2 | 140 | 118 | 90 |
| 11 | 22.2 | 143 | 108 | 92 |
| 12 | 22.1 | 144 | 117 | 95 |
| 13 | 21.2 | 137 | 106 | 91 |
| 14 | 22.3 | 118 | 103 | 72 |
| 15 | 18.1 | 128 | 110 | 105 |

(III) Cardiac Activity

Rat hearts were perfused by the Langendorff procedure.

Hearts were dissected free within 30 seconds of death and reverse perfused via the aorta and coronary vessels with Krebs-Ringer bicarbonate solution (pH 7.4, 37° C.) gassed with 95% oxygen:5% carbon dioxide at a flow rate between 8–12 cm$^3$/minute. Responses were observed after injection of drug dissolved in isotonic saline into the perfusion media. Heart rate and tension were displayed on a Ormed MX2P recorder via a tension transducer and heart ratemeter.

Results are expressed as a percentage of the maximum response due to salbutamol.

| COMPOUND OF EXAMPLE NO. | DOSE ADDED TO PERFUSATE ($\mu$g) | HEART TENSION | HEART RATE |
| --- | --- | --- | --- |
| Salbutamol | | 100 | 100 |
| 1 | 30 | 0 | 33 |
| 2 | 30 | 5 | 57 |
| 3 | 30 | 14 | 36 |
| 4 | 30 | 40 | 88 |
| 5 mp 114–20 | 30 | 0 | 0 |
| 5 mp 102–5 | 30 | 25 | 0 |
| 6 | 30 | 10 | 0 |
| 7 | 30 | 11 | 33 |
| 8 | 30 | 10 | 0 |
| 9 | 30 | 20 | 0 |
| 10 | 30 | 10 | 0 |
| 11 | 30 | 90 | 0 |
| 12 | 30 | 8 | 0 |

(IV) Hypoglycaemic Activity

Female CFLP mice, weighing approximately 25 g, were fasted for 24 hours prior to the study. The compounds under study were administered orally as an aqueous solution to each of 8 mice. 30 minutes later a blood sample (20 $\mu$m$^3$) was obtained from the tail for the analysis of blood glucose. Immediately after taking this blood sample, glucose (1 g/kg body weight) was administered subcutaneously to each mouse. 8 mice were given water as a control. Blood samples were then obtained from each mouse at 30 minute intervals for 120 minutes.

Compounds that produced a significant (P<0.05) reduction on blood glucose, compared with control mice given water, at any time interval, were considered active. The area under the blood glucose curve over the 2 hour period after the administration of the glucose was calculated for each compound and compared with the value for control animals.

| COMPOUND OF EXAMPLE NO. | DOSE ($\mu$mol/kg) | REDUCTION IN AREA UNDER BLOOD GLUCOSE CURVE (%) |
| --- | --- | --- |
| 2 | 2.6 | 11 |
| 3 | 2.6 | 56 |
| 4 | 1 | 18 |
| 11 | 1 | 41 |
| 12 | 1 | 28 |
| 13 | 12.5 | 45 |
| 14 | 12.5 | 35 |
| 15 | 2.5 | 27 |

(V) Anti-Inflammatory Activity

The method used is based on that described by G. Tonelli et al (Endocrinology, 77, 625–634, 1965). An inflammation is induced in the rat ear by the application of 50 $\mu$l of a 1% solution of croton oil in tetrahydrofuran, test compounds being dissolved in the irritant vehicle. After 6 hours the inflammation is assessed by killing the animals and weighing the ears. Topical anti-inflammatory activity of a compound is generally considered to be shown when a significant (5% level) reduction in ear weight is seen compared to non-drug treated control.

| COMPOUND OF EXAMPLE NO. | DOSE mg/RAT EAR | ACTIVITY |
| --- | --- | --- |
| 5 mp 102–5 | 2.0 | Active |

(VI) Platelet Aggregation Inhibition Activity

Male CFLP mice (ca 20 g, n=8) were dosed orally with compound or vehicle (controls) after an overnight fast. Two hours later each mouse received an intravenous dose of collagen (400 $\mu$g/kg, pH 6–6.6). Exactly 30 sec. after injection of collagen, each mouse was placed in a chamber of $CO_2$ until respiration ceased. Blood platelet concentration was determined (Ultra-Flo 100 whole blood platelet counter, Clay Adams) in blood samples (3 $\mu$l) taken immediately from the inferior vena cava. Each concentration was expressed as a percent of that obtained in a tail blood sample taken immediately before injection of collagen. Results are given in the table below.

| COMPOUND | Dose p.o. $\mu$mol(mg)/kg | % Inhibition of response to collagen. |
| --- | --- | --- |
| Aspirin | 600(108) | 29 p < 0.05 |
| Example 3 | 5(1.92) | 29 p = 0.01 |

I claim:

1. A method for treating obesity in humans or domestic animals comprising administering to an obese human or domestic mammal an effective, non-toxic amount of a compound of formula (I)

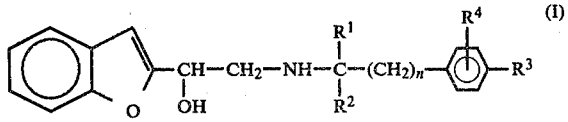

wherein
- $R^1$ is hydrogen or methyl;
- $R^2$ is hydrogen or methyl;
- $R^3$ is hydroxy, hydroxy ($C_{1-6}$) alkoxy, benzyloxy or a group

X—Y—Z wherein
    (i) X is a bond, Y is $C_{1-6}$ straight or branched alkylene or $C_{2-6}$ straight or branched alkenylene, and Z is hydrogen or carboxy or —$COR^5$ in which $R^5$ is $C_{1-6}$ straight or branched alkoxy or —$NR^6R^7$ in which $R^6$ and $R^7$ are the same or different and each is selected from hydrogen and $C_{1-6}$ straight or branched alkyl; or
    (ii) X is oxygen, Y is $C_{1-6}$ straight or branched alkylene and Z is carboxy or —$COR^5$ in which $R^5$ is $C_{1-6}$ straight or branched alkoxy or —$NR^6R^7$ in which $R^6$ and $R^7$ are the same or different and each is selected from hydrogen and $C_{1-6}$ straight or branched alkyl; or
    (iii) X is —O—$CH_2$—, Y is $C_{2-6}$ straight or branched alkenylene and Z is carboxy or —$COR^5$, $R^5$ is $C_{1-6}$ straight or branched alkoxy or —$NR^6R^7$ and $R^6$ and $R^7$ are the same or different and each is selected from hydrogen and $C_{1-6}$ straight or branched alkyl,
- $R^4$ is selected from hydrogen, hydroxy, halogen, $C_{1-6}$ straight or branched alkyl or $C_{1-6}$ straight or branched alkoxy; and n is 1, 2 or 3 or a pharmaceutically acceptable salt thereof.

2. A method of treating hyperglycaemia in humans or domestic mammals comprising administering to a hyperglycaemic human or domestic mammal an effective, non-toxic amount of a compound of formula (I)

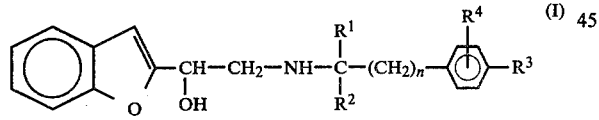

wherein
- $R^1$ is hydrogen or methyl;
- $R^2$ is hydrogen or methyl;
- $R^3$ is hydroxy, hydroxy ($C_{1-6}$) alkoxy, benzyloxy or a group

X—Y—Z wherein:
    (i) X is a bond, Y is $C_{1-6}$ straight or branched alkylene or $C_{2-6}$ straight or branched alkenylene, and Z is hydrogen or carboxy or —$COR^5$ in which $R^5$ is $C_{1-6}$ straight or branched alkoxy or —$NR^6R^7$ in which $R^6$ and $R^7$ are the same or different and each is selected from hydrogen and $C_{1-6}$ straight or branched alkyl; or
    (ii) X is oxygen, Y is $C_{1-6}$ straight or branched alkylene and Z is carboxy or —$COR^5$ in which $R^5$ is $C_{1-6}$ straight or branched alkoxy or —$NR^6R^7$ in which $R^6$ and $R^7$ are the same or different and each is selected from hydrogen and $C_{1-6}$ straight or branched alkyl; or
    (iii) X is —O—$CH_2$—, Y is $C_{2-6}$ straight or branched alkenylene and Z is carboxy or —$COR^5$, $R^5$ is $C_{1-6}$ straight or branched alkoxy or —$NR^6R^7$ and $R^6$ and $R^7$ are the same or different and each is selected from hydrogen and $C_{1-6}$ straight or branched alkyl,
- $R^4$ is selected from hydrogen, hydroxy, halogen, $C_{1-6}$ straight or branched alkyl or $C_{1-6}$ straight or branched alkoxy; and n is 1, 2 or 3 or a pharmaceutically acceptable salt thereof.

3. A method of treating inflammation in humans and domestic mammals comprising administering to a human or domestic mammal suffering from inflammation an effective, non-toxic amount of a compound of formula (I)

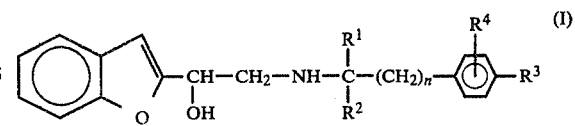

wherein
- $R^1$ is hydrogen or methyl;
- $R^2$ is hydrogen or methyl;
- $R^3$ is hydroxy, hydroxy ($C_{1-6}$) alkoxy, benzyloxy or a group

X—Y—Z wherein:
    (i) X is a bond, Y is $C_{1-6}$ straight or branched alkylene or $C_{2-6}$ straight or branched alkenylene, and Z is hydrogen or carboxy or —$COR^5$ in which $R^5$ is $C_{1-6}$ straight or branched alkoxy or —$NR^6R^7$ in which $R^6$ and $R^7$ are the same or different and each is selected from hydrogen and $C_{1-6}$ straight or branched alkyl; or
    (ii) X is oxygen, Y is $C_{1-6}$ straight or branched alkylene and Z is carboxy or —$COR^5$ in which $R^5$ is $C_{1-6}$ straight or branched alkoxy or —$NR^6R^7$ in which $R^6$ and $R^7$ are the same or different and each is selected from hydrogen and $C_{1-6}$ straight or branched alkyl; or
    (iii) X is —O—$CH_2$—, Y is $C_{2-6}$ straight or branched alkenylene and Z is carboxy or —$COR^5$, $R^5$ is $C_{1-6}$ straight or branched alkoxy or —$NR^6R^7$ and $R^6$ and $R^7$ are the same or different and each is selected from hydrogen and $C_{1-6}$ straight or branched alkyl,
- $R^4$ is selected from hydrogen, hydroxy, halogen, $C_{1-6}$ straight or branched alkyl or $C_{1-6}$ straight or branched alkoxy; and n is 1, 2 or 3 or a pharmaceutically acceptable salt thereof.

4. A method for inhibiting platelet aggregation in humans and domestic mammals in need of such treatment, comprising administering an effective, non-toxic amount of a compound of formula (I)

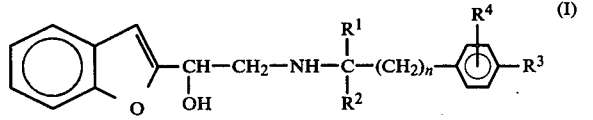

wherein
- $R^1$ is hydrogen or methyl;
- $R^2$ is hydrogen or methyl;
- $R^3$ is hydroxy, hydroxy ($C_{1-6}$) alkoxy, benzyloxy or a group

X—Y—Z wherein:
(i) X is a bond, Y is $C_{1-6}$ straight or branched alkylene or $C_{2-6}$ straight or branched alkenylene, and Z is hydrogen or carboxy or —$COR^5$ in which $R^5$ is $C_{1-6}$ straight or branched alkoxy or —$NR^6R^7$ in which $R^6$ and $R^7$ are the same or different and each is selected from hydrogen and $C_{1-6}$ straight or branched alkyl; or (ii) X is oxygen, Y is $C_{1-6}$ straight or branched alkylene and Z is carboxy or —$COR^5$ in which $R^5$ is $C_{1-6}$ straight or branched alkoxy or —$NR^6R^7$ in which $R^6$ and $R^7$ are the same or different and each is selected from hydrogen and $C_{1-6}$ straight or branched alkyl; or (iii) X is —O—$CH_2$—, Y is $C_{2-6}$ straight or branched alkenylene and Z is carboxy or —$COR^5$, $R^5$ is $C_{1-6}$ straight or branched alkoxy or —$NR^6R^7$ and $R^6$ and $R^7$ are the same or different and each is selected from hydrogen and $C_{1-6}$ straight or branched alkyl, $R^4$ is selected from hydrogen, hydroxy, halogen, $C_{1-6}$ straight or branched alkyl or $C_{1-6}$ straight or branched alkoxy; and n is 1, 2 or 3 or a pharmaceutically acceptable salt thereof.

* * * * *